United States Patent [19]

Karami

[11] 4,047,528

[45] Sept. 13, 1977

[54] DISPOSABLE DIAPER WITH RETAINING AND SECURING FASTENER

[75] Inventor: Hamzeh Karami, Crystal Lake, Ill.

[73] Assignee: Colgate-Palmolive Company, New York, N.Y.

[21] Appl. No.: 715,782

[22] Filed: Aug. 19, 1976

[51] Int. Cl.² .......................................... A61F 13/16
[52] U.S. Cl. ................................ 128/287; 128/290 R
[58] Field of Search .................. 128/284, 287, 290 R, 128/291

[56] References Cited

U.S. PATENT DOCUMENTS

| 3,616,114 | 10/1971 | Hamaguchi | 128/287 X |
|---|---|---|---|
| 3,930,502 | 1/1976 | Tritsch | 128/287 |
| 3,948,267 | 4/1976 | Karami | 128/287 |
| 3,978,861 | 9/1976 | Schaar | 128/287 |

*Primary Examiner*—Aldrich F. Medbery
*Attorney, Agent, or Firm*—Powell L. Sprunger

[57] ABSTRACT

A disposable diaper comprising, an absorbent pad assembly having a pair of side edges, a pair of end edges connecting the side edges, a front surface, a backing sheet of fluid impervious material defining a back surface of the pad assembly, an absorbent pad, and a laterally extending end section adjacent one end edge of the pad assembly. The diaper has a tape fastener comprising, a release sheet having a release back surface and being attached to the back surface of the end section adjacent the side edge of the pad assembly. The fastener has a securement section having adhesive on a front surface releasably attached to the back surface of the release sheet and having a release back surface. The fastener also has a retaining section having adhesive on a front surface releasably attached to the back surface of the securement section.

11 Claims, 11 Drawing Figures

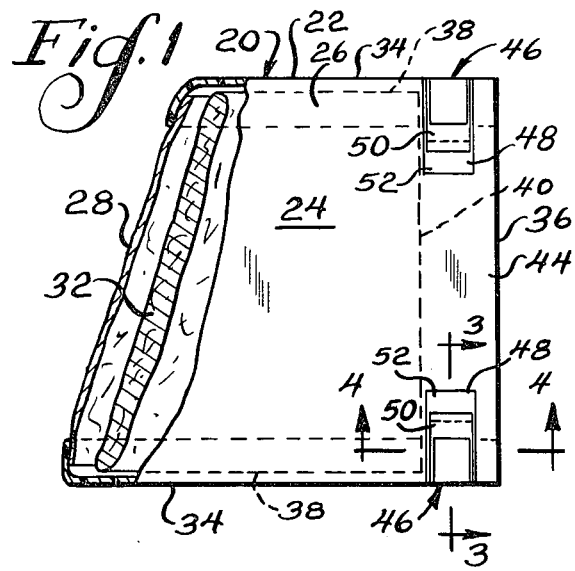
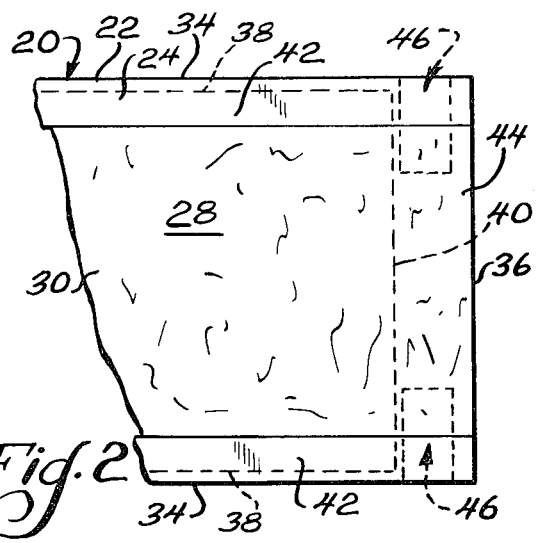
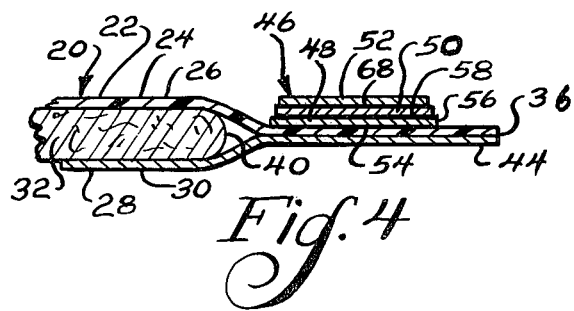
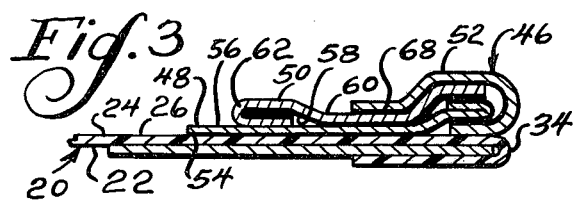
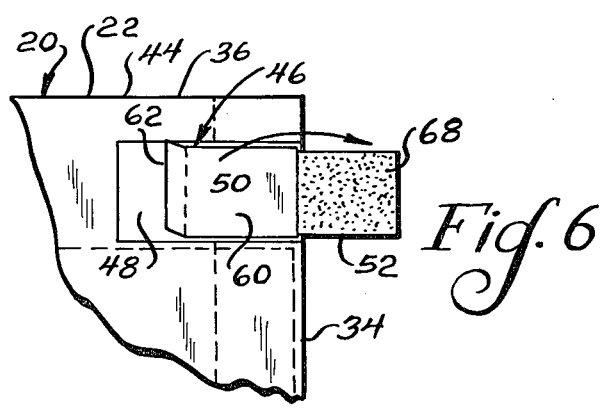
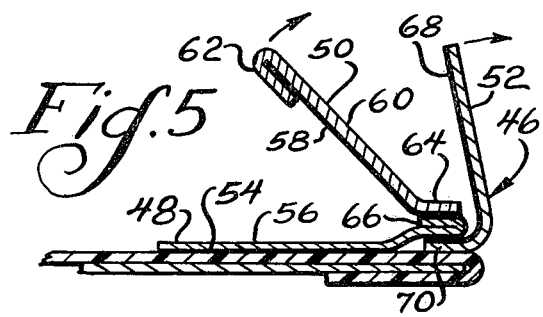
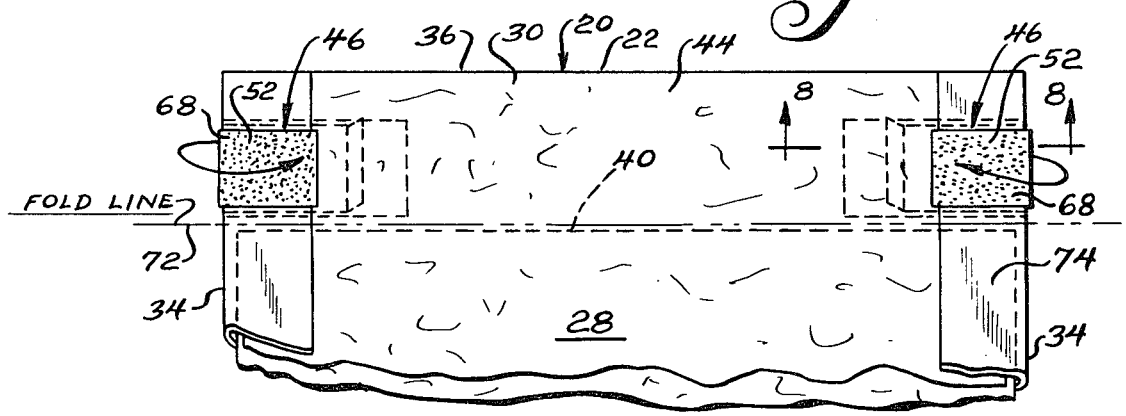

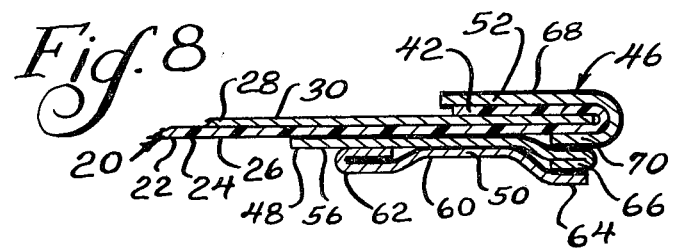
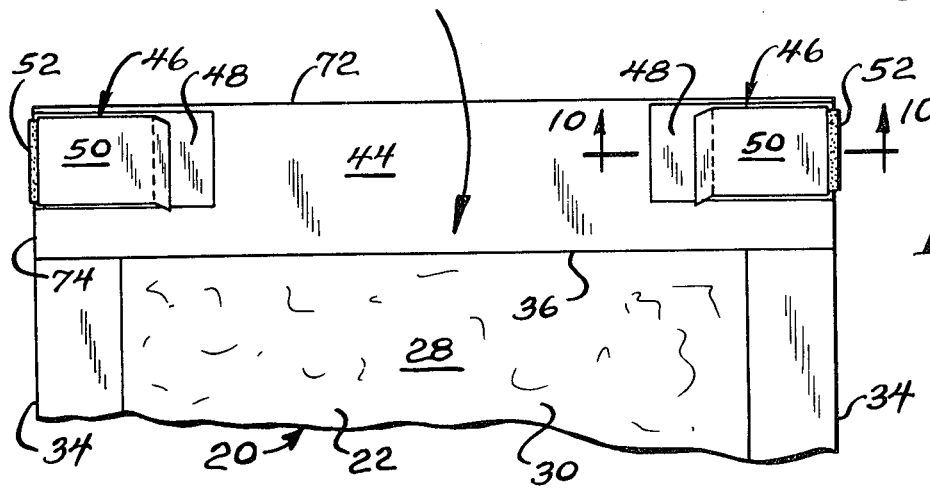
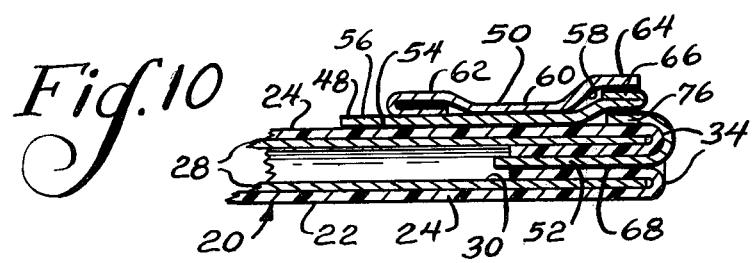
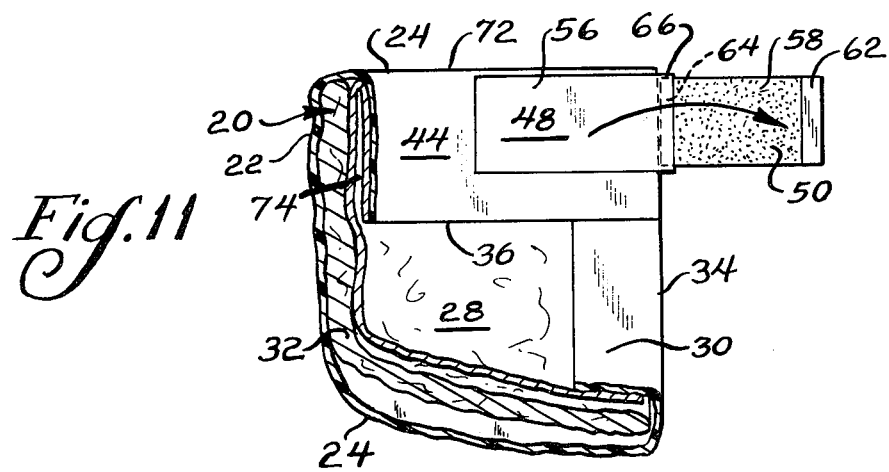

DISPOSABLE DIAPER WITH RETAINING AND SECURING FASTENER

BACKGROUND OF THE INVENTION

The present invention relates to absorbent articles, and more particularly to disposable diapers.

A various assortment of disposable diapers have been proposed for use on infants, and have become increasingly popular with parents since they may be discarded after a single use and need not be laundered. Such diapers are normally constructed having a fluid impervious backing sheet, a fluid pervious top or cover sheet, and an absorbent pad intermediate the backing and cover sheets. The diapers have also been provided with tape fasteners normally having a securement portion having adhesive covered with a release sheet.

One of the problems associated with such diapers has been recurrent leakage from the absorbent pad in the waistline portion. Further, it is desirable that the release sheets of such fasteners are not separated from the diaper when removed from the securement portions, since such loose release sheets must be discarded by the parents during placement of the diaper, thus causing inconvenience of necessary disposal.

SUMMARY OF THE INVENTION

A principal feature of the present invention is the provision of a disposable diaper having an improved tape fastener.

The diaper of the present invention comprises, an absorbent pad assembly having a pair of side edges, a pair of end edges connecting the side edges, a front surface, a backing sheet of fluid impervious material defining a back surface of the pad assembly, an absorbent pad, and a laterally extending end section adjacent one end edge of the pad assembly. The diaper has a tape fastener comprising, a release sheet having a release back surface and being attached to the back surface of the end section adjacent a side edge of the pad assembly. The fastener has a securement section having adhesive on a front surface releasably attached to the back surface of the release sheet and having a release back surface. The fastener also has a retaining section having adhesive on a front surface releasably attached to the back surface of the securement section. The retaining section may be peeled from the securement section and folded around the side edge of the pad assembly into a configuration with the retaining section overlying the front surface of the pad assembly and with the adhesive on the retaining section facing away from the front surface of the pad assembly. The end section of the pad assembly may be folded over an adjacent portion of the pad assembly into a configuration with the adhesive on the retaining section contacting a portion of the pad assembly underlying the end section.

A feature of the present invention is that the retaining section retains the end section of the pad assembly in its overlying configuration.

Another feature of the present invention is that the end section of the pad assembly may overlie an end portion of the pad and prevent fluid leakage from a waistline of the diaper.

Still another feature of the present invention is that the securement section may be removed from the release sheet and unfolded into a configuration extending past a side edge of the pad assembly for securing the diaper about an infant.

Yet another feature of the present invention is that the fastener eliminates the necessity of discarding separate release sheets during placement of the diaper.

Further features will become more fully apparent in the following description of the embodiments of this invention and from the appended claims.

DESCRIPTION OF THE DRAWINGS

In the drawings:

FIG. 1 is a fragmentary back plan view of a disposable diaper having a tape fastener according to the present invention;

FIG. 2 is a fragmentary front plan view of the diaper of FIG. 1;

FIG. 3 is a fragmentary sectional view taken substantially as indicated along the line 3—3 of FIG. 1;

FIG. 4 is a fragmentary sectional view taken substantially as indicated along the lines 4—4 of FIG. 1;

FIG. 5 is a fragmentary section view illustrating components in the tape fastener of the present invention;

FIG. 6 is a fragmentary back plan view illustrating a retaining section of the tape fastener being unfolded about a side edge of the diaper pad assembly;

FIG. 7 is a fragmentary front plan view of the diaper illustrating the retaining sections as folded around the front surface of the pad assembly;

FIG. 8 is a fragmentary sectional view taken substantially as indicated along the line 8—8 of FIG. 7;

FIG. 9 is a fragmentary front plan view illustrating an end section of the pad assembly as folded over a front surface of an adjacent portion of the pad assembly;

FIG. 10 is a fragmentary sectional view taken substantially as indicated along the line 10—10 of FIG. 9; and FIG. 11 is a fragmentary front plan view of the diaper illustrating a securement section as unfolded for securing the diaper about an infant.

DESCRIPTION OF THE PREFERRED EMBODIMENTS

Referring now to FIGS. 1—5, there is shown a disposable diaper generally designated 20 having an absorbent pad assembly 22. The pad assembly 22 has a fluid impervious backing sheet 24, such as polyethylene, defining a back surface 26 of the pad assembly, a fluid pervious cover or top sheet 28, such as a nonwoven material, defining a front surface 30 of the pad assembly 22, and an absorbent pad 32, such as comminuted wood pulp termed in the art as fluff, located intermediate the backing sheet 24 and cover sheet 28. The pad assembly 22 has a pair of side edges 34, and end edges 36 connecting the side edges 34. The absorbent pad 32 also has a pair of side edges 38 and end edges 40 connecting the side edges 38. In a preferred form, as shown, the side edges 38 of the pad 32 are located adjacent the side edges 34 of the pad assembly 22, and the fluid impervious backing sheet has lateral side margins 42 folded over and secured to the top sheet 28, such that the backing sheet side margins 42 cover lateral side margins of the absorbent pad 32. Also, as shown, the end edge 40 of the pad 32 is spaced inwardly from the end edge 36 of the pad assembly 22, and the backing sheet 24 and cover sheet 28 define an end portion or section 44 of the pad assembly located intermediate the end edge 40 of the pad 32 and the end edge 36 of the pad assembly 22 in a waistline portion of the diaper.

As best shown in FIGS. 3-5, the diaper 20 has a tape fastener generally designated 46 having a release sheet 48, a securement section 50, and a retaining section 52. The release sheet 48 has adhesive 54 on the front surface secured to the back surface 26 of the end section 44 adjacent the side edge 34 of the pad assembly 22, and has a release back surface 56. In a suitable form, the back surface 56 of the release sheet 48 may be treated to provide the release properties, such as a silicone release coating on a paper release sheet, or the release sheet may comprise a strip of polyethylene such that the back surface of the polyethylene release sheet provides moderate affinity for selected adhesive.

The securement section 50 has adhesive 58 on the front surface, and has a release back surface 60. The release surface 60 may be formed in a manner similar to the release back surface of the release sheet 48, and the securement section 50 may be selected from similar materials, as desired. The securement section 50 may have a folded over end defining a tab 62 at the outer end to facilitate removal of the securement section 50 from the release sheet 48. Also, the adhesive 58 on an inner end 64 of the securement section 50 may be attached to the adhesive 54 on a folded back inner end 66 of the release sheet 48, such that the inner ends 64 and 66 of the securement section 50 and release sheet 48, respectively, are attached together. With reference to FIGS. 3 and 4, the adhesive 58 on the front surface of the securement section 50 is releasably attached to the back release surface 56 of the release sheet 48 in a folded configuration of the tape fastener.

The retaining section 52 has adhesive 68 on the front surface, and has an inner end 70 folded beneath the release sheet 48, with the adhesive 68 on the inner end 70 of the retaining section 52 being secured to the adhesive 54 of the release sheet 48 beneath the folded back inner end 66 of the release sheet 48. In this manner, the release sheet 48, diaper portion securement section 50, and retaining section 52 are joined together at their inner ends. With reference to FIGS. 3 and 4, the adhesive 68 on the retaining section 52 is releasably attached to the back release surface 60 of the securement section 50, and, if desired, the retaining section 52 may have a tab at its outer end to facilitate removal from the securement section 50.

The tape fastener 46 is maintained in the folded configuration shown in FIGS. 1–4 prior to use of the diaper. When it is desired to place the diaper on an infant, with reference to FIG. 6, the retaining section 52 is peeled from the release back surface 60 of the securement section 50, and folded toward the side edge 34 of the pad assembly 22. With reference to FIG. 7, the retaining sections 52 are folded around the side edges 34 of the pad assembly 22 into a configuration overlying the front surface 30 of the pad assembly 22 and end section 44. In this configuration, as shown in FIGS. 7 and 8, the adhesive 68 on the retaining sections 52 face away from the front surface 30 of the pad assembly 22, while the securement section 50 remains releasably attached to the back release surface 56 of the release sheet 48. Next, with reference to FIGS. 7, 9, and 10, the end section 44 of the pad assembly is folded about a laterally extending fold line 72 over the front of the pad assembly 22, such that the front surface 30 of the end section 44 faces the front surface 30 of an adjacent portion 74 of the pad assembly. At this time, the adhesive 68 on the retaining sections 52 contact the front surface of the pad assembly in the adjacent underlying portion 74, and retain the end section 44 in its configuration overlying the adjacent portion 74. In a preferred form, as shown, the fold line 72 is located adjacent the end edge 40 of the absorbent pad 32 and intermediate the end edge 40 of the absorbent pad and the end edge 36 of the pad assembly 22, such that the end section 44 overlies and covers an end margin of the absorbent pad. In this manner, the tape fastener 46 is used to retain the end section 44 in its overlying configuration, and the fluid impervious backing sheet defining the back surface of the end section 44 provides an end barrier to prevent leakage from the absorbent pad in the waistline portion of the pad assembly during use of the diaper.

Finally, with reference to FIG. 11, the securement section 58 is peeled from the back release surface 56 of the release sheet 58, and unfolded into a configuration extending past the side edge 34 of the pad assembly 22. In this configuration, the securement section 50 is utilized to attach the tape fastener to a remote portion of the diaper during placement in order to secure the diaper about an infant.

In accordance with the present invention, the tape fastener 46 retains the end section 44 in an overlying configuration forming a fluid impervious barrier at the end of the diaper, and provides a securement section for securing the diaper about an infant. Additionally, the release sheet 48 is anchored to the end section 44 of the pad assembly 22, and eliminates the necessity of discarding separate release sheets during placement of the diaper.

The foregoing detailed description is given for clearness of understanding only, and no unnecessary limitations should be understood therefrom, as modifications will be obvious to those skilled in the art.

I claim:
1. A disposable diaper, comprising:
   an absorbent pad assembly having a pair of side edges, a pair of end edges connecting the side edges, a front surface, a backing sheet of fluid impervious material defining a back surface of the pad assembly, an absorbent pad, and a laterally extending end section adjacent one end edge of the pad assembly; and
   a tape fastener comprising, a release sheet having a release back surface and being attached to the back surface of said end section adjacent a side edge of the pad assembly, a securement section having adhesive on a front surface releasably attached to the back surface of the release sheet and having a release back surface, and a retaining section having adhesive on a front surface releasably attached to the back surface of the securement section, said retaining section being peeled from the securement section and folded around the side edge of the pad assembly into a configuration with the retaining section overlying the front surface of the pad assembly and with the adhesive on the retaining section facing away from the front surface of the pad assembly, said end section of the pad assembly being folded over an adjacent portion of the pad assembly into a configuration with the adhesive on the retaining section contacting a portion of the pad assembly underlying the end section and retaining the end section in the overlying configuration, and said securement section being peeled from the release sheet to secure the diaper about an infant.

2. The diaper of claim 1 wherein said pad has an end edge spaced from the one end edge of the pad assembly, and said end section is folded about a fold line located intermediate said end edge of the pad and the one end edge of the pad assembly.

3. The diaper of claim 2 wherein said fold line is located adjacent said end edge of the pad.

4. The diaper of claim 1 wherein inner ends of the release sheet and the securement section are attached together.

5. The diaper of claim 1 wherein inner ends of the release sheet and the retaining section are attached together.

6. The diaper of claim 1 wherein said backing sheet defines the back surface of said end section.

7. The diaper of claim 6 wherein said end section overlies an end portion of the absorbent pad.

8. A disposable diaper, comprising:
an absorbent pad assembly having a pair of side edges, a pair of end edges connecting the side edges, a front surface, a backing sheet of fluid impervious material defining a back surface of the pad assembly, an absorbent pad, and a laterally extending end section adjacent one end edge of the pad assembly, said end section being folded over an adjacent portion of the pad assembly; and a tape fastener comprising, a release sheet having a release back surface and being attached to the back surface of said end section adjacent a side edge of the pad assembly, a retaining section extending from the back surface of the end section around the side edge of the end section and having adhesive on a front surface attached to the front surface of said adjacent portion of the pad assembly to retain the end section in a configuration overlying said adjacent portion, and a securement section having adhesive releasably attached to the back surface of the release sheet and being unfolded into a configuration extending past the side edge of the end section after removal from the release sheet.

9. The diaper of claim 8 wherein said backing sheet defines the back surface of the end section, and in which the end section overlies an end portion of the pad.

10. The diaper of claim 8 in which inner ends of the release sheet, retaining section and securement section are joined adjacent the side edge of the end section.

11. A disposable diaper, comprising:
an absorbent pad assembly having a pair of side edges, a pair of end edges connecting the side edges, a front surface, a backing sheet of fluid impervious material defining a back surface of the pad assembly, an absorbent pad, and a laterally extending end section adjacent one end edge of the pad assembly, said end section being folded over an adjacent portion of the pad assembly;

a tape fastener comprising, a release sheet having a release back surface and being attached to the back surface of said end section adjacent a side edge of the pad assembly, and a securement section having adhesive releasably attached to the back surface of the release sheet and being unfolded into a configuration extending past the side edge of the end section after removal from the release sheet; and means for retaining the end section of the pad assembly in the folded configuration overlying said adjacent portion of the pad assembly.

* * * * *